(12) United States Patent
Frank et al.

(10) Patent No.: US 7,510,682 B2
(45) Date of Patent: Mar. 31, 2009

(54) TEST ELEMENT ANALYSIS SYSTEM

(75) Inventors: Martin Frank, Dirmstein (DE); Michael Fritz, Biblis (DE); Frank Deck, Niederkirchen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 884 days.

(21) Appl. No.: 10/696,360

(22) Filed: Oct. 29, 2003

(65) Prior Publication Data

US 2004/0141881 A1 Jul. 22, 2004

(30) Foreign Application Priority Data

Oct. 29, 2002 (DE) ................................ 102 50 331

(51) Int. Cl.
*G01N 33/49* (2006.01)
(52) U.S. Cl. .......................................... 422/63; 422/55
(58) Field of Classification Search .................. 422/50, 422/52, 55–58, 60–61, 63, 104
See application file for complete search history.

(56) References Cited

U.S. PATENT DOCUMENTS

| | | | |
|---|---|---|---|
| 2,608,433 A * | 8/1952 | Marbeuf ..................... 294/99.2 |
| 3,932,133 A | 1/1976 | Ishikawa ....................... 33/16 |
| 4,118,280 A | 10/1978 | Charles et al. .............. 195/127 |
| 4,876,204 A | 10/1989 | Inoue et al. .................... 436/46 |
| 5,075,079 A * | 12/1991 | Kerr et al. ...................... 422/64 |
| 5,143,694 A | 9/1992 | Schafer et al. ................ 422/65 |
| 5,173,261 A | 12/1992 | Krause et al. ................. 422/58 |
| 5,258,163 A | 11/1993 | Krause et al. ................. 422/58 |
| 5,332,549 A | 7/1994 | MacIndoe, Jr. ............... 422/63 |
| 5,507,388 A * | 4/1996 | Kildal et al. ............. 206/459.5 |
| 6,176,119 B1 | 1/2001 | Kintzig ..................... 73/53.01 |

FOREIGN PATENT DOCUMENTS

| | | | |
|---|---|---|---|
| EP | 0285851 | 3/1988 | |
| EP | 0312394 A2 | 10/1988 | .................... 33/53 |
| EP | 0654668 | 11/1994 | |
| EP | 0823635 A2 | 8/1997 | ................... 33/487 |
| GB | 2014113 A | 1/1978 | |

* cited by examiner

*Primary Examiner*—Jill Warden
*Assistant Examiner*—Natalia Levkovich
(74) *Attorney, Agent, or Firm*—Baker & Daniels LLP

(57) ABSTRACT

This invention relates to test element analysis system for the analytical investigation of body liquids. An evaluation instrument, pertaining to the system, comprises a storage container, where a plurality of test elements is held ready for use, a sample application position, where one test element at a time is brought into contact with the sample, a measuring device for the determination of a measurable variable characteristic for the analysis, and a transport device, by which one test element at a time is taken out of the test element storage container at the take out position and transported to the sample application position.

10 Claims, 6 Drawing Sheets

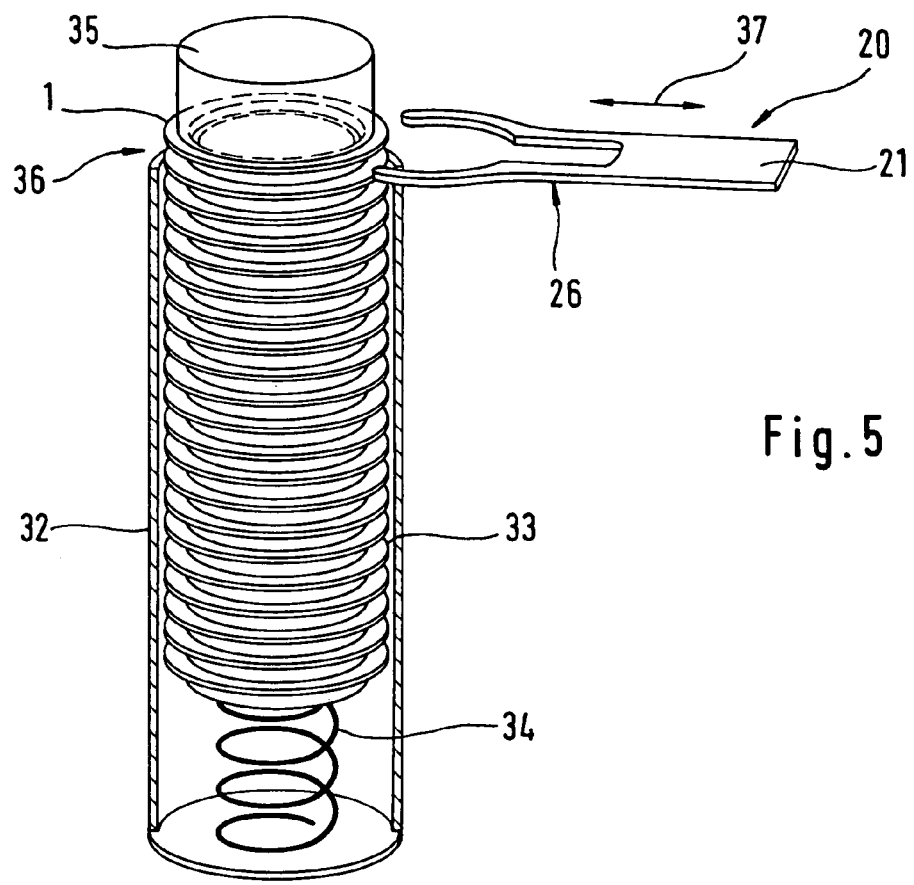
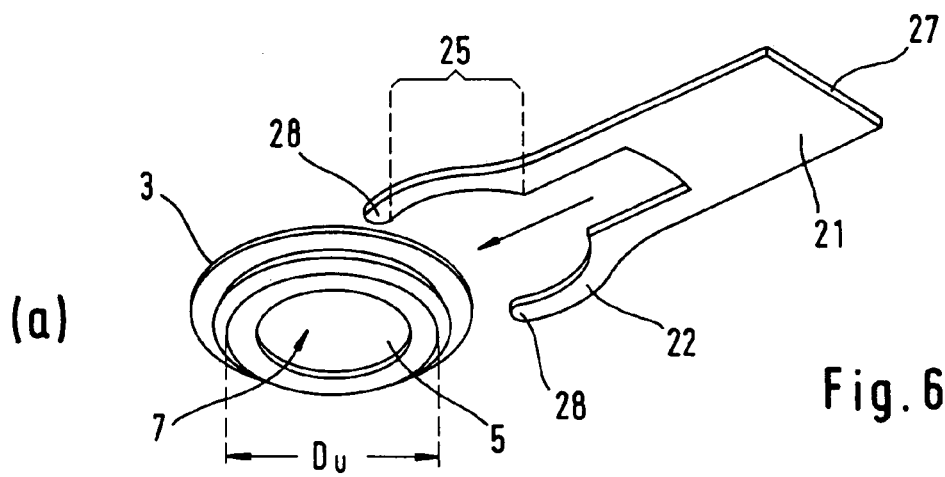
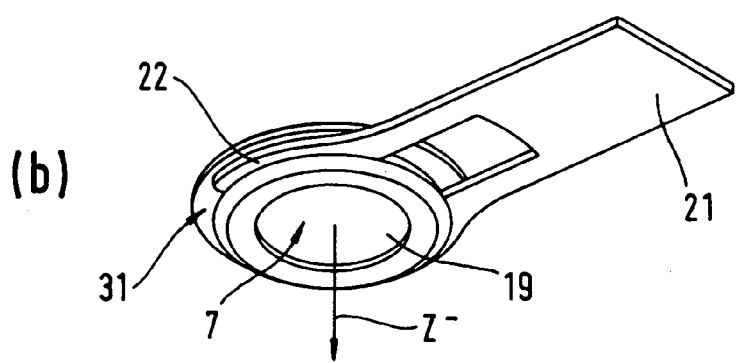
Fig. 5
Fig. 6

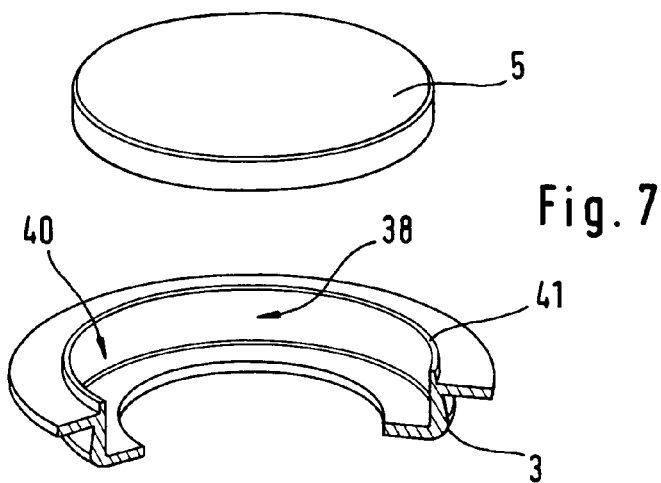
Fig. 7
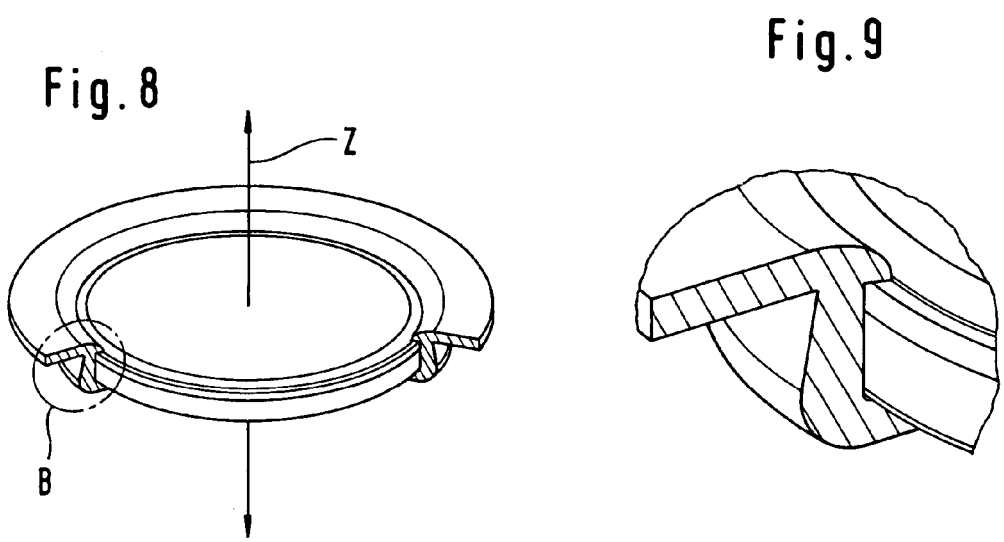
Fig. 8
Fig. 9
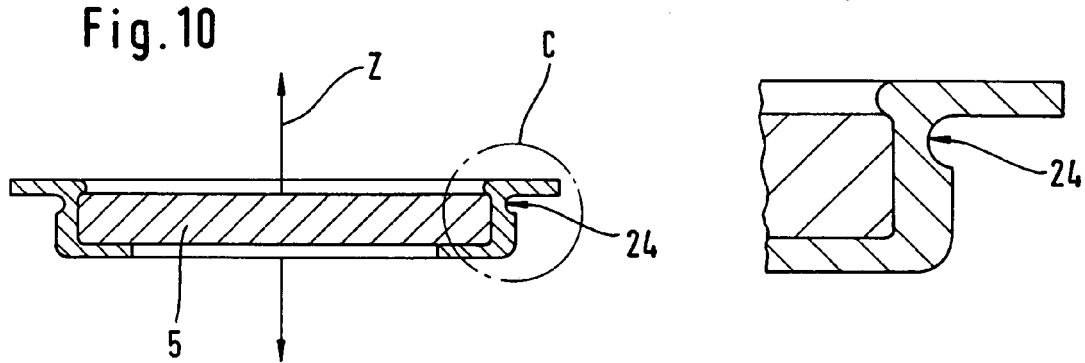
Fig. 10
Fig. 11

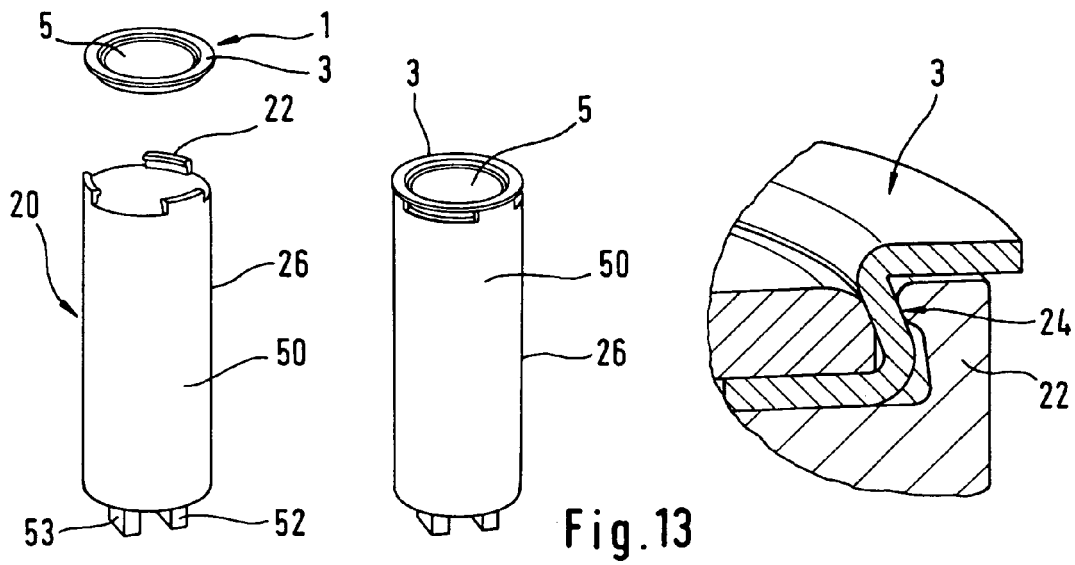
Fig.12  Fig.13  Fig.14
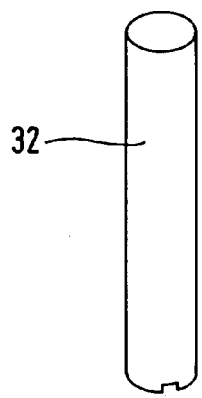
Fig.15
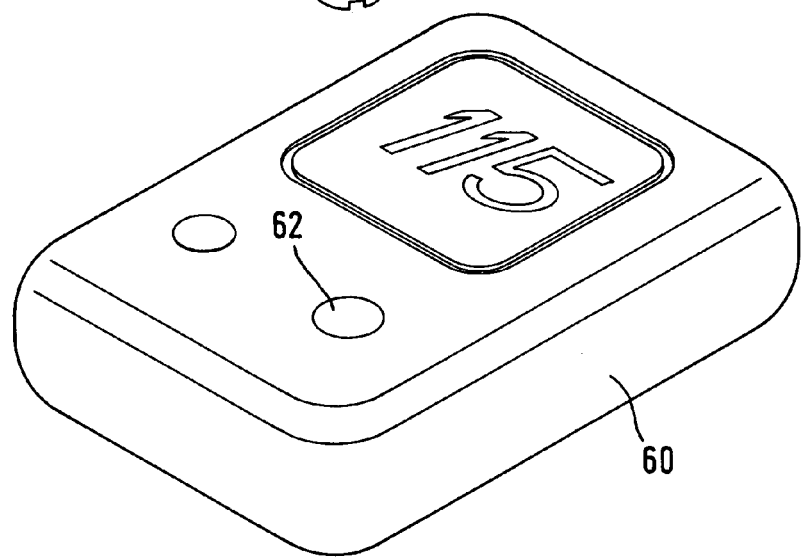

TEST ELEMENT ANALYSIS SYSTEM

RELATED APPLICATION

This application claims priority to German Application No. DE 10250331.1 filed Oct. 29, 2002.

TECHNICAL FIELD

This invention relates to a test element analysis system for the analytical investigation of a liquid sample as well as to test elements for such an analysis system and to a method for the production thereof.

BACKGROUND

Test procedures operating with test elements are used on a large scale to analyze the components in a liquid sample qualitatively and quantitatively, particularly in body fluids of humans or animals. These test elements contain reagents. For the execution of a reaction, the test element is brought into contact with the sample. The reaction of sample and reagent leads to a change of the test element which is characteristic for the analysis, and is evaluated by means of an appropriate evaluation instrument. Generally, the evaluation instrument is appropriate for the evaluation of a certain type of test elements of a certain manufacturer. The test elements and the evaluation instrument are components which are mutually adapted to each other and together designated as analysis system.

Numerous test element types are known, which can be differentiated by the measuring principle, the used reagents as well as by their structure.

With respect to the measuring principle, colorimetric analysis systems are used very frequently. Here the reaction of the sample with the reagents contained in the test element leads to a color change which can be measured visually, or by using a photometric measuring device. Furthermore, electrochemical analysis systems have obtained high importance, wherein the reaction of the sample with the reagents of the test elements leads to an electrically measurable change (of an electrical voltage or an electrical current), to be measured by means of corresponding electronic measuring system.

With respect to the structure, strip-shaped analysis elements (test strips) are particularly common, consisting of an elongated carrier layer made of plastic material, and test fields fixed onto this carrier layer. Generally, the test fields consist of test layers which contain one or more reagents. Such test strips are particularly used, to a large extent, for blood and urine investigations.

A second type of test elements, which so far is used only to a small extent in practice, has a test field surrounded by a frame, similar to a photographic diapositive. In the English literature, such test elements are called "analysis slides". The test field of this test element type generally consists of one or more test layers supported by the frame and containing reagents appropriate for colorimetric tests. After the application of the sample to the test field and the process of the test reaction, a color generation can be observed, or photometrically measured, on the opposite side (generally the underside) of the test field. Such test elements with frames are known, for example, from U.S. Pat. No. 5,173,261.

Furthermore, special forms of test elements have been proposed for special applications. For example, EP 0312394 A2 describes a test element for immunochemical tests, wherein a membrane, containing immunochemical substances, is mounted in a plastic part shaped as a truncated cone. The plastic part is attached to a syringe in order to aspire a liquid through the membrane by means of the syringe plunger, thus enabling the separation of bound and free reagent components which is required in this type of test.

In most cases, test element analyses are performed manually. However, numerous analysis systems have been proposed, wherein the analysis is partially or completely automatic. The evaluation instruments of such systems generally contain the following subunits: a test element storage container, in which a plurality of test elements is stored, a sample application location at which the test element is brought into contact with the sample, a measuring device for measuring the change of a test element which is characteristic for the analysis, the test element being located in a measuring position (which may coincide with or be different from the sample application position), and a transport facility which takes one test element at a time from the test element storage container, transports it to the sample application device, and—if necessary—further transports it, after contacting with the sample, to the measuring position.

Very different proposals have been made with respect to the constructive design. For example, U.S. Pat. Nos. 3,932,133 and 4,876,204 describe evaluation instruments wherein the test element storage container is shaped as a magazine in which a plurality of test strips are stored in a stacked manner, one upon the other. In order to take the test strips out of the container and to transport them to the subsequent processing stations, a transport device with a gripper, taking up one test stripe at a time, is provided.

In GB 2014113 A, EP 0054849 and U.S. Pat. No. 5,143,694, different developments are described, which have in common that test strips are transported, by means of a transport device, continuously in a direction transversal to their longitudinal direction, passing the necessary processing stations. To this end GB 2014113 uses a cylinder, EP 0054849 uses a continuously transporting paper strip, and U.S. Pat. No. 5,143,694 uses a system of transport fingers, which push the test strips, via rails within a plastic insert, from an application position via a measuring station to a waste deposit.

All these automatically working test element analysis systems need much space. They are constructively expensive and need relatively much electrical energy. Therefore, they are not appropriate for small, portable battery-operated analysis systems, as they are common for the blood sugar home monitoring of diabetics.

In order to allow a simplified handling in the field of blood sugar home monitoring, EP 0823635 proposes a special form of test elements wherein the test field is integrated into the front face of a carrier element which is shaped as a truncated cone or a truncated pyramid. A plurality of test elements is stacked, one upon the other, in a tube-shaped magazine and stored ready for use in such a manner that a correspondingly designed evaluation instrument can be attached to the respective upper test element in the magazine. To this end a projection of the test element latches into a corresponding recess at the head of the evaluation instrument, thus providing a connection between the test element and the evaluation instrument. Subsequently, the test element fixed to the device is brought into contact with a drop of blood, produced, for example, at the finger tip. The sophisticated form of these test elements causes substantial costs. Nevertheless, handling is not substantially simplified as compared to conventional test strips.

EP 0922959 describes an analysis system which comprises a damp-proof storage container for test elements and an evaluation instrument. The evaluation instrument is equipped with two guiding grooves, namely one guiding groove adapted to a corresponding profile of the test elements, and a second guiding groove, acting together with a corresponding guiding element of the storage container. In order to take a test element from the storage container and to place it into the test element holder of the evaluation instrument, both components are joined, resulting in a direct take-over of a test element from the storage container into the instrument. This facilitates the handling. The design, however, is relatively expensive, and the material consumption for the production of the test elements is relatively high. On this basis, the invention addresses the problem to create a test element analysis system wherein a handling improvement, in particular with respect to the removal of the test elements from a storage container and their transport to a sample application position of the evaluation instrument, is achieved with a low expense. The design shall be simple and must be appropriate for small, portable, battery-operated analysis systems.

SUMMARY

According to a first main aspect of the invention, this problem is solved by a test element analysis system which comprises test elements with a test field, which—for the purpose of performing an analysis—is brought in contact with a sample, wherein the reaction of one of the analytes contained in the sample with at least one of the reagents contained in the test element leads to a change of a measurable variable which is characteristic for the analysis. The system also comprises an evaluation instrument with a test element storage container, in which a plurality of test elements are stored ready for use at a take out position, a sample application position, at which the test field of a respective test element is brought into contact with the sample, a transport device, transporting one test element at a time from the take out position of the test element storage container and to the sample application position, and a measuring device, used to measure the measurable variable characteristic for the analysis of a test element. The test elements comprise a frame at least partially surrounding the test field and having an outwardly oriented gripping rim running around the outer circumference of the frame and the transport device comprises a gripping device for taking up one test element at a time, one test element at a time being held at the gripping rim during at least a part of the transport path from the take out position to the sample application position.

According to a second main aspect of the invention, the problem is solved by a test element analysis system, comprising test elements with the previously explained characteristics, a test element storage container in which a plurality of test elements are stored to be taken out at a take out position of the storage container, and an evaluation instrument with a test element holder for positioning one test element at a time in a sample application position, at which its test field is brought into contact with the sample, and with a measuring device for measuring the measurable variable characteristic for the analysis, wherein the test elements comprise a frame at least partially surrounding the test field with an outwardly oriented circumferential gripping rim running around the outer circumference of the frame, wherein the diameter of the frame increases from the gripping rim in both spatial directions ($Z^+$ and $Z^-$) vertical to the test field plane, and wherein the system includes a gripping device, which holds during the take out from the storage container one test element at a time at its gripping rim.

The invention also refers to test elements appropriate for such test element analysis systems, as well as a method for the production thereof.

The invention is appropriate for calorimetric as well as for electrochemical analysis systems. The term "test field" is used herein to designate the area of the test element which is brought into contact with the sample and is wetted by the sample. It is not necessarily a design element which is separate from the surrounding frame. For electrochemical test elements, in particular, it is useful if the test field and the frame are made of a single-piece plastic part, wherein the necessary electrodes are integrated on or in the test field surface. In every case, the frame which surrounds the test field at least partially, is not wetted by the sample and includes the circumferential gripping rim at its outer circumference.

The invention achieves substantial advantages: The test elements can be produced easily and cheaply. The frame, favorably made from metal or from a plastic material (preferable containing polycarbonate or a polyester), can have a very thin and narrow shape. This does not only reduce the amount of material needed, but also the packaging volume of the test elements; i.e. a large quantity of test elements can be stored in a magazine with relatively small volume. The space requirements for a waste deposit appropriate for receiving used test elements are also reduced; The transport device for automatic evaluation instruments can be of a very simple design with a minimum of moving parts; A partial mechanization of the handling steps by using a system comprising a special storage container and a corresponding evaluation instrument as functionally adapted elements (see EP 0922959) is also possible with lower expense; At the same time a reliable function is achieved. This is particularly true if the cross sectional profile of the frame is shaped, in the area of the gripping rim, in such a manner that the connection between the gripping arms and the test element is not only frictional, but positive locking. In practice, this is achieved by the fact that the frame diameter increases from the gripping surface in at least one direction running perpendicular to the test field plane, forming a protruding shoulder.

BRIEF DESCRIPTION OF THE DRAWINGS

The invention is hereafter described in more detail with reference to exemplary embodiments schematically shown in the figures. The described features can be used individually or in combination in order to create preferred embodiments of the invention. In the figures.

FIG. 5 shows a perspective illustration of a gripping arm taking out a test element according to FIGS. 2 to 4 from a tube-shaped magazine.

FIG. 6 shows a perspective illustration of two moving phases (a) and (b) during the process of gripping a test element by means of a gripping arm.

FIG. 7 shows an illustration corresponding to FIG. 2 of a further alternative embodiment of a test element.

FIG. 8 shows a partially sectional illustration of the test element according to FIG. 7 with inserted and fixed test field.

FIG. 9 shows a detailed illustration of section B of FIG. 8.

FIG. 10 shows a section through the frame of a further alternative embodiment of a test element.

FIG. 11 shows a detailed illustration of section C of FIG. 10.

FIG. 12 shows a perspective illustration of an alternative embodiment of a gripping device with a test element not yet gripped.

FIG. 13 shows a perspective illustration of the gripping device according to FIG. 11 with gripped test element.

FIG. 14 shows a detailed illustration for the explanation of the cooperation of the gripping arms and the gripping rim in the embodiment of FIGS. 12 and 13, FIG. 15 shows a perspective illustration of a partially mechanized analysis system.

DETAILED DESCRIPTION

Figure 1:
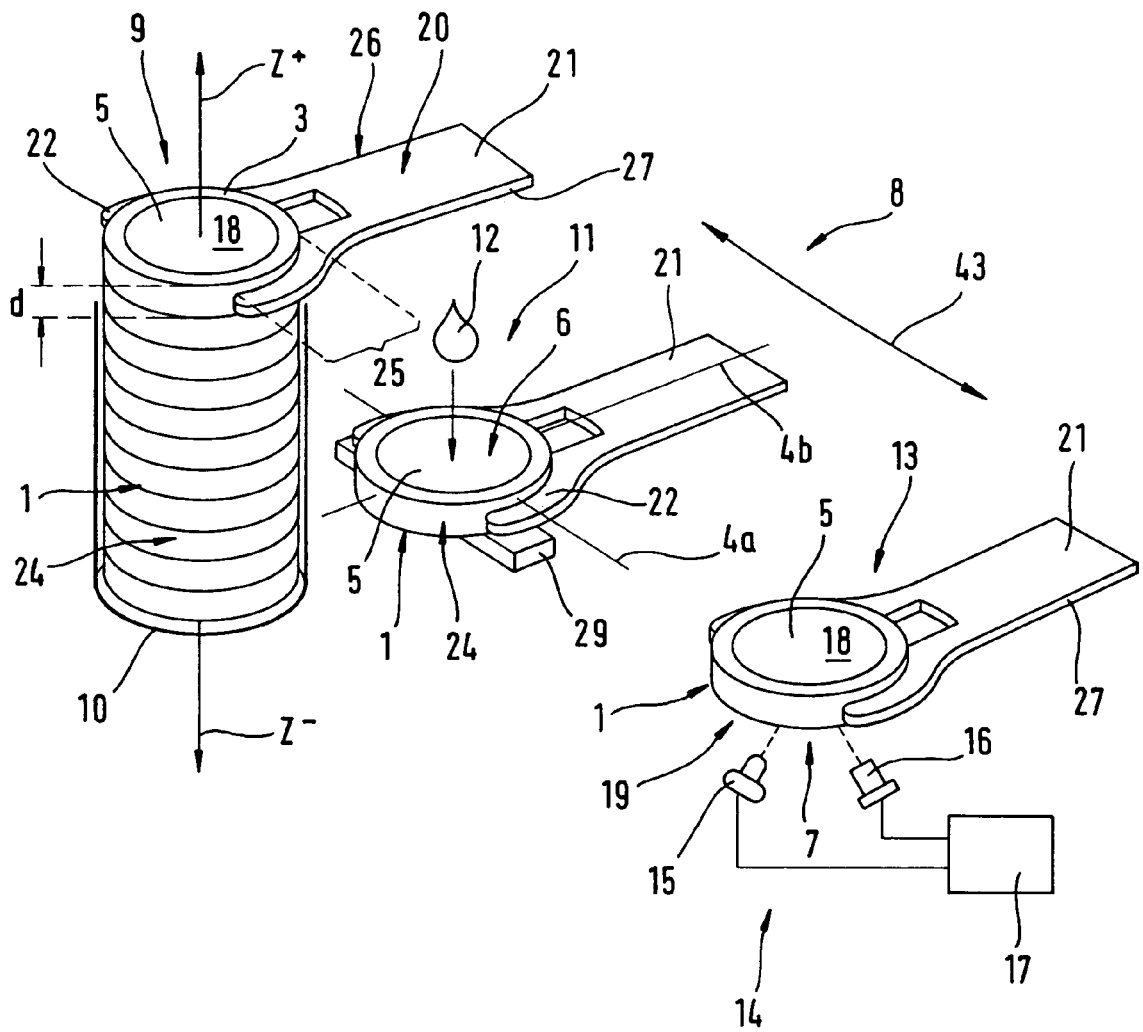
FIG. 1 shows a perspective principal sketch of the movement of a gripping device for the transport of a test element between three functional positions of an evaluation instrument.

The following description of the preferred embodiment is merely exemplary in nature and is in no way intended to limit the invention or its application or uses.

The test elements 1 shown in the figures respectively comprise a frame 3 surrounding a test field aperture 2 and a test field 5 arranged in the test field aperture 2. The test field 5 defines a test field plane (in the figures illustrated by two straight lines 4a and 4b).

In all embodiments shown in the figures, the test field consists of a single layer or of a compound of several mutually fixed layers (normally containing different reagents). Generally, the invention can also be used with test fields which consist of a plurality of loose layers. Such a plurality of layers can be fixed and held together by the frame 3, as described, for example, in U.S. Pat. No. 5,173,261. As already mentioned, embodiments wherein the test field and the frame are not separated parts, are also possible, in particular for electrochemical test elements.

The test elements 1 are disk-shaped in the sense that their thickness d in axial direction Z is much smaller than its dimensions in the spatial directions running perpendicular thereto. The shown shape of the test elements 1, which is circular in top view onto the test field plane (in particular rotation-symmetric), is preferred, however, not absolutely necessary. The test elements 1 may rather have an outer limitation different from the circular shape. Therefore, the concept "disk-shaped" must not be understood in a limiting way in the sense of "circular disk shaped".

An at least central-symmetrical shape with a curved limitation (for example, an elliptic or an oval shape) is preferred. Such a geometry, preferably a circular geometry, offers a series of substantial advantages: The holding of round test elements in the gripping device is self-centering, the design of the storage container in form of a magazine (FIG. 5) is easier and the relation between the sample application surface area 18 and the overall area of the test element 1 is particularly advantageous. Generally, however, a rectangular or even asymmetrical shape of the test elements 1 is possible.

Here the Z direction running perpendicular to the test field plane (which in case of a rotation-symmetric test element coincides with its axis of symmetry) is designated "axial direction", even for non-rotation-symmetric test elements. Similarly the designation "radial" is used for a spatial direction parallel to the test field plane, away from the center of the test field 5 (or from its border towards the center).

The liquid sample is applied to a sample application side 6 of the test element 1. It penetrates into the test field and reacts with the reagents contained therein. For the shown calorimetric test, the reaction leads to a photometrically measurable color change which is characteristic for the analysis, in an evaluation zone of the test field on the evaluation side 7 of the test element 1, opposite to the sample application side 6.

Within the evaluation instrument, not shown completely in FIG. 1, the test elements 1 are moved between various functional positions by means of a transport device 8. Three functional positions are shown in FIG. 1, namely a take out position 9, where a test element is taken from a storage container 10 preferably shaped as a magazine (here only schematically shown), a sample application position 11, where the test element 1 is brought into contact with the sample 12, and a measuring position 13, where a measurable variable which is characteristic for the analysis, is measured by means of a measuring device 14. In the shown case, this is a reflection-photometric measuring device with a light emitter 15, a light receiver 16 and a measuring and evaluation electronics 17. By these means the diffuse reflection of the evaluation zone 19 (in the shown case, the lower side of the test field 5) is measured in generally known manner.

The transport device 8 grips and transports one test element 1 at a time by means of a gripping device 20, here embodied as gripping fork 21 with two arms 22. The area of the frame where it is contacted by the arms is designated gripping rim 24. It is formed by a surface at the outer circumference of the frame 3 which is directed radially towards the outside, i.e. away from the test field center and runs around at least a part of the circumference. The section of the arms 22, where the contact to the gripping rim 24 takes place, is designated gripping section 25. In the gripping section 25, the gripping arms 22 can be in contact to the gripping rim 24 of the frame 3, either continuously or point-by-point. The gripping section 25 is the part of the arms 22 between the first and the last contact point. It runs parallel to the test field plane 4.

By using a gripping device 20 which is embodied as a gripping fork 21, a particularly space-saving and reliable design is obtained. It is possible to provide the entire transport of the test elements 1 between the functional positions of the evaluation instrument by means of a simple swiveling movement of the gripping fork 21 around a fixed axis.

As opposed to the known grippers used in automatic test element analysis systems, the gripping device 21 does not contact the upper and lower side of a carrier layer which has a large surface area, but instead it contacts a small gripping rim from the outside. As the holding force is directed in radial direction from the outside to the inside, the gripping device 20 may also be designated radial gripper.

The thickness of the test elements 1 (i.e. their maximal dimension in axial direction) is preferably less than 3 mm. In order to ensure a secure hold by means of the narrow gripping rim 24, the thickness should be at least 0.3 mm. Preferably, the thickness is 0.5 mm to 1 mm.

In the shown preferred embodiment, the frame surface (the surface area of the frame seen in top view onto the test field plane) is smaller, at least not much larger, than the sample application surface 18 of the test field 5. Preferably, the frame surface is at most three times as large as the sample application surface 18 of the test field. Test elements 1 with a narrow frame are characterized by a low material consumption for the production. Furthermore they can be stored in a very space-saving way. This is even more true due to the generally small dimensions of the test elements according to the invention. Preferably, the largest dimension of the test elements in radial direction (in case of round test elements, their diameter) is smaller than 10 mm, preferably smaller than 6 mm. During practical testing of the invention, analysis elements with only about 4 mm of external diameter, and a diameter of the sample application surface 18 of 3 mm (i.e. a frame width of 0.5 mm) were used.

Generally, each of the gripping arms 22 can be connected to the rest of the gripping device 20 by means of a swiveling bearing, and can be mechanically movable. However, an embodiment is preferred, wherein the mobility necessary for gripping and holding the test elements 1 is based on the fact that the arms 22 are elastically connected to the gripping device 20, in such a manner that they can be pushed—only due to this elasticity (i.e. without the necessity to move the arms 22 of the gripping fork 21 by means of an operating mechanism)—onto or around the test element, so that the test element is held thereby. Preferably, the elastic movability results from an intrinsic elasticity of the gripping element 26, here embodied by the gripping fork 21. With other words the gripping element 26, including the arms 22, is elastically deformable with respect to a movement parallel to the test field plane, and is formed in such a manner that it is submitted to a bending force when a test element 1 is carried thereby. As shown, the arms 22 of a gripping fork 21 preferably are part of a single-piece fork part 27, made of an elastic material (metal or plastic) for example by pressing or punching.

In order to improve a secure holding of the test elements 1, the gripping arms 22 are preferably shaped—as shown—in such a manner that the distance between each other decreases towards the front end 28 of the gripping section 25. With such a design the gripping rim 24 of a round test element 1 is surrounded by the arms 22 by more than 180 degrees. By this design feature the fixing of the test element 1, in particular against slipping out due to a movement parallel to the test field plane, is improved.

In the embodiment shown in FIG. 1, the gripping rim 24 is formed by a cylinder surface running straight in axial direction Z. With respect to a displacement in Z direction, the test element is only fixed by frictional force. The holding force generated thereby can be insufficient under certain circumstances, for example if a blood drop is applied in the sample application position 11, and the user simultaneously presses (accidentally) against the test element 1. In order to avoid the falling out of the test element 1 from the gripping fork 21 in such a case, an additional support 29 can be provided in the instrument, which supports the test element 1 when it is in the sample application position 11.

FIGS. 2 to 11 show preferred embodiments, wherein an improved fixing of the test elements 1 in the gripping device 20 is achieved due to the shape of the profile of the frame 3 in the area of the gripping rim 24. These embodiments have in common that the diameter of the frame 3 increases from the gripping rim 24 towards both directions $Z^+$ and $Z^-$ perpendicular to the test field plane 4a, 4b (thus, for the horizontal position of the test elements 1 shown in the figures, in upward and downward direction). Therefore, the gripping rim is located, seen from axial direction Z, at the point of the smallest diameter of the limiting surface, directed radially to the outside, of the frame 3. Thereby, a positively locking fixing of the test elements 1 in the gripping device 20 is achieved with respect to both axial spatial directions $Z^+$ and $z^-$.

A first embodiment of such test elements is shown in FIGS. 2 to 7. Above the gripping rim 24, the frame 3 widens thereby forming a flange-like shoulder 31. The material of the shoulder 31 should be (at least at the surface of the sample application side 6) hydrophobic (if necessary, hydrophobized by a surface treatment) in order to optimize the hygienic effectiveness. Preferably, the shoulder 31 is wide enough to cover, at least partially, preferably completely, neighboring parts of the gripping device 20 (here, the gripping section 25 of the arms 22 contacting the gripping rim 24). By this design, a contamination of these parts, and thus of the evaluation instrument, during the application of the sample 12 in the sample application position 11, is avoided reliably and with simple means.

In downward direction (in direction $Z^-$) the diameter of the frame 3 of the gripping rim 24 increases only slightly. This shallow profile is sufficient to ensure the necessary fixing of the test element 1 against slipping out from the gripping fork 21 in upward direction (in $Z^+$ direction).

Figure 2:
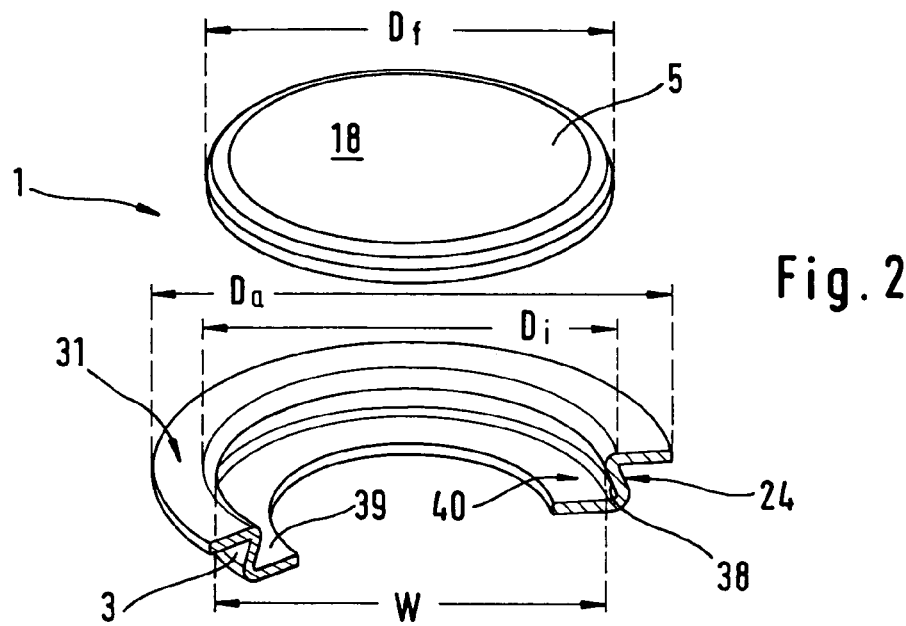
FIG. 2 shows a perspective, partially sectional illustration of an alternative embodiment of a test element.
Figure 3:
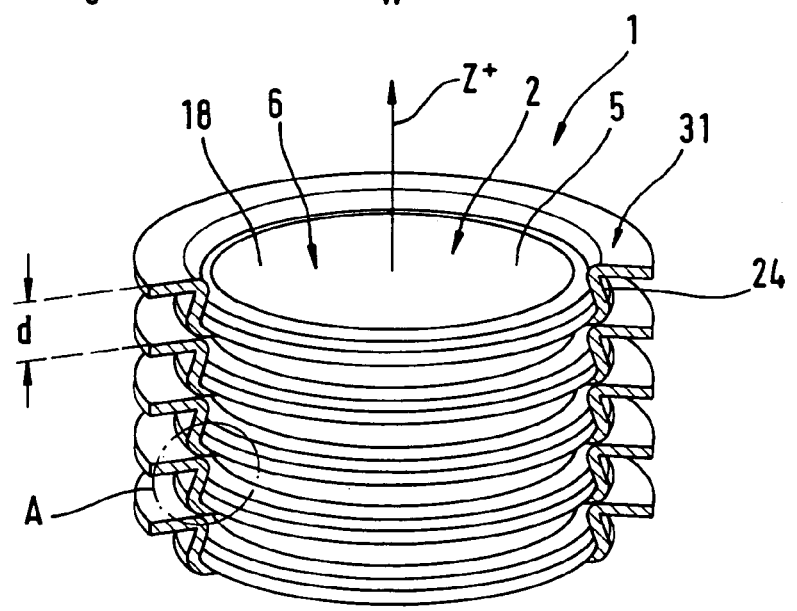
FIG. 3 shows a perspective, partially sectional illustration of a stack of test elements according to FIG. 2.
Figure 4:
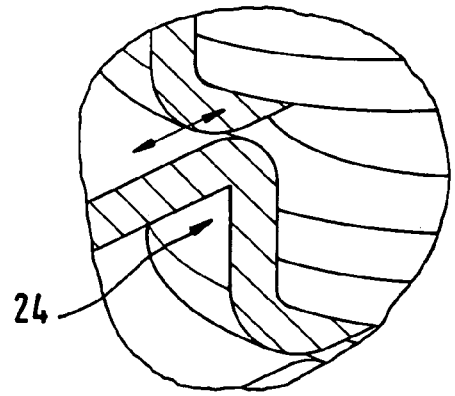
FIG. 4 shows a detailed illustration of section A of FIG. 3.

During the conception of the profile of the frame 3, well to be seen in FIGS. 2 and 4, it must also be considered that the sectional shape of the test element 1 should preferably be such that a plurality of test elements 1, stacked one upon the other, can slide without interlocking on each other in the direction of the test field plane 4a, 4b. Thereby among other things, the test elements 1 can be pulled or pushed out of a magazine 32 without the necessity of further moving parts.

Such a removal process is shown schematically in FIG. 5. The test elements 1 are stacked directly one upon the other in a storage container 10, embodied here as a tube-shaped magazine. In order to allow to take the test elements out successively at the same take out position, by the translatory removal movement indicated by arrow 37, the stack 33 of the test elements 1 is pressed, for example by a spring 34, in upward direction against a fixed counterpiece 35. The take out slot remaining between the counterpiece 35 and the upper limitation of the casing of the magazine 32 is a little higher than the thickness d of a test element, thus allowing to take out one test element at a time by a gripping fork 21.

In order to enable this operation, the test elements 1 must be able to slide on one another in stacked state. This sliding ability is supported by the shown profile of the frame, which is characterized in that on one side (here, the sample application side 6) its interior dimension $D_i$ is smaller, but its exterior dimension $D_a$ is larger, than the exterior dimension $D_u$ (FIG. 6) of the opposite side (which has to slide upon the first side; here, the evaluation side 7) (i.e. $D_i<D_u<D_a$). With such a shape test elements 1 stacked one upon the other have an annular physical contact to each other. Due to the resulting advantageous pressure distribution, the risk of test elements 1 being stuck together during a longer storage period, is reduced.

The profile of the frame 3 is important, also with respect to a simple and reliable fixing of the test field 5 in the frame 3. If a test field 5 produced separately from the frame 3 is used, the frame 3 is preferably shaped in such a manner that it encloses a reception trough 40 for accepting the test field 5, and that the depth of the reception trough 40 is bigger than the thickness of the test field 5, so that the circumferential limiting wall 38 of the reception trough 40 surpasses the surface of an inserted test field 5. Due to this feature, the test field 5 does not come in contact with neighboring test elements of a test element stack.

In the embodiment shown in FIGS. 2 to 7, the limiting walls 38 of the reception trough 40 have a negative ascent at the lower partial section of their height dimension (i.e. they are inclined to the inside, seen in upward direction), so that the diameter of the reception trough 40 at their bottom 39 is larger than above the bottom. The test field 5 is fixed in the test field reception trough 40 due to the fact that the clear width W (minimum dimension in a plane parallel to the test field plane) of the test field reception trough 40 is a little smaller than the diameter $D_f$ of the test field, so that the test field is slightly compressed in radial direction during the insertion into the reception trough 40. The material of the test field 5 is sufficiently elastic to expand again after the insertion into the reception trough 40, and to be fixed in a snug fit in the reception trough 40.

Preferably, the storage container 10 is closed as tight as possible, in order to increase the storage life of moisture-sensitive test elements. For a magazine of the constructive type shown in FIG. 5, a sufficient sealing effect can be obtained by an adaptation of the interior diameter to the exterior diameter of the test elements 1 and by a corresponding design of the counterpiece 35. Generally, the test element storage container may be open, for example if the test elements do not react sensitively to environmental influences or if the storage container is located in a sealed instrument housing.

FIGS. 7 to 9 show an embodiment particularly appropriate in cases where the material of the test field 5 is not sufficiently elastic to be fixed in the frame 3 in the previously described manner. Here the fixing is achieved by beading a fixing edge 41 supplied at the border of the test field trough 40, from the position shown in FIG. 7 to the position shown in FIG. 8. This requires that the frame 3 is made of a plastically deformable material, as e.g. metal. However, plastic materials can be processed in this way, too.

In the embodiment shown in FIGS. 10 and 11, the principle of fixing the test field 5 is the same as in FIGS. 2 to 6. The profile, however, is different in the area of the gripping rim 24, in so far that the gripping rim 24 is formed by a groove-shaped recess concavely curved in section.

A particular advantage of the shown embodiment is that the transport between the functional positions necessary in the evaluation instrument is possible with very few simple mechanical movements. The gripping of a test element 1 requires only one simple translatory relative motion (arrow 37 in FIG. 5) of the gripping fork 21 towards the stack of test elements 1 (or alternatively, of the stack of test elements 1 towards the gripping fork 21). Subsequently, a simple transversal movement—once again parallel to the test field plane (arrow 43 in FIG. 1)—is sufficient to transport the test element to the further functional stations. This movement can be realized, for example, as a swiveling movement of the gripping fork 21 around a stationary axis. Thereby a complete automation of the analysis process in an evaluation instrument is possible in a simple way, even if the instrument has very compact dimensions and is battery-operated.

In the embodiment shown in FIGS. 12 to 14, the gripping element 26 of the gripping device 20 is shaped as elongated gripping tube 50 with short arms 22 protruding from the upper end of the gripping tube. With respect to the test field 5 of the test element 1, the arms 22 extend in vertical direction to the test field plane (thus, in Z direction). Again, the necessary mobility of the arms 22 is based on the intrinsic elasticity of the gripping element 26, formed in this case by the gripping tube 50. In this case, too, the arms 22 are elastically deformable, with respect to a movement parallel to the test field plane, in such a manner that the gripping tube can be pushed, by an upward movement in Z direction, over the frame 3 of the test element 1, the arms 22 holding the test element 1 by contacting its gripping rim 24.

Such an embodiment is advantageous for calorimetric analysis systems, because waveguides 52,53 can be integrated into the gripping tube, serving for coupling the light in and out. In case of electrochemical analysis systems, the necessary electrical contacts can be integrated into the gripping arms, both in this embodiment and in the previously shown embodiments. Another advantage of embodying the gripping device 20 as gripping tube 50, is for certain shapes of the instrument the geometry, which is space-saving in radial direction.

In the embodiments shown, the gripping device 20 is in contact to the gripping rim 24 via gripping arms 22. However, embodiments are also possible wherein the gripping device does not comprise (elastically suspended) gripping arms, but wherein, by a relative displacement of moving parts, the gripping rim is surrounded in such a manner that fixing is obtained by positive locking.

As already explained, the invention is not only advantageous for a fully automatic analysis system (as shown in FIG. 1), but also in case of a partially mechanized analysis system. Here the explained design of the test element can be used advantageously in combination with a corresponding gripping device to take out test elements from a storage container forming part of the system (in particular, a magazine), and to insert the elements into a corresponding element holder of the corresponding evaluation instrument. Particularly preferred is an embodiment (in this respect corresponding to EP 0922959) wherein the gripping device is a part of the evaluation instrument, and wherein the test element is taken over directly from the take out position of the storage container to the evaluation instrument.

Figure 16:
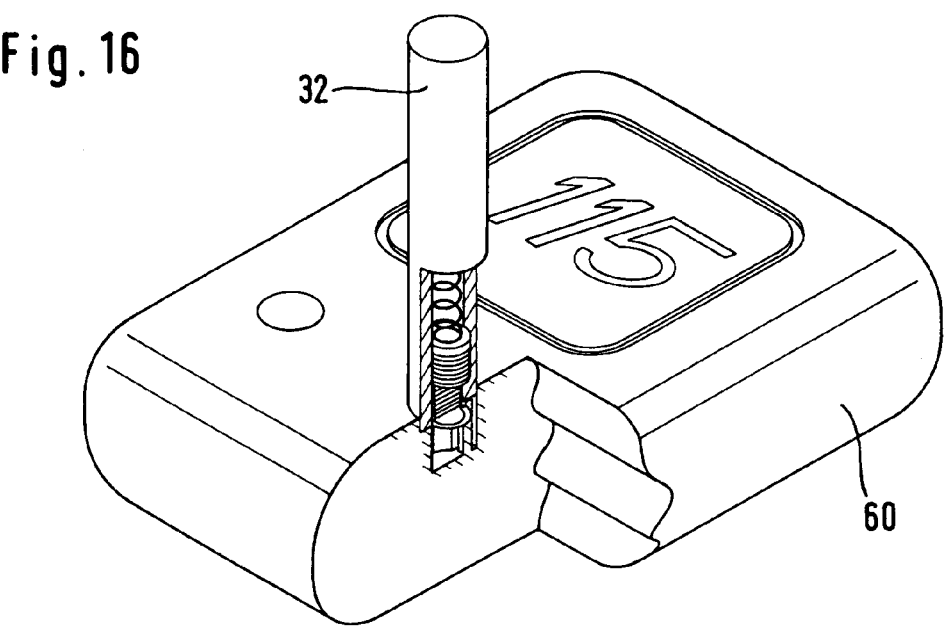
FIG. 16 shows a perspective, partially sectional illustration of the system according to FIG. 15 during the take-over of a test element from a magazine into the evaluation instrument.
Figure 17:
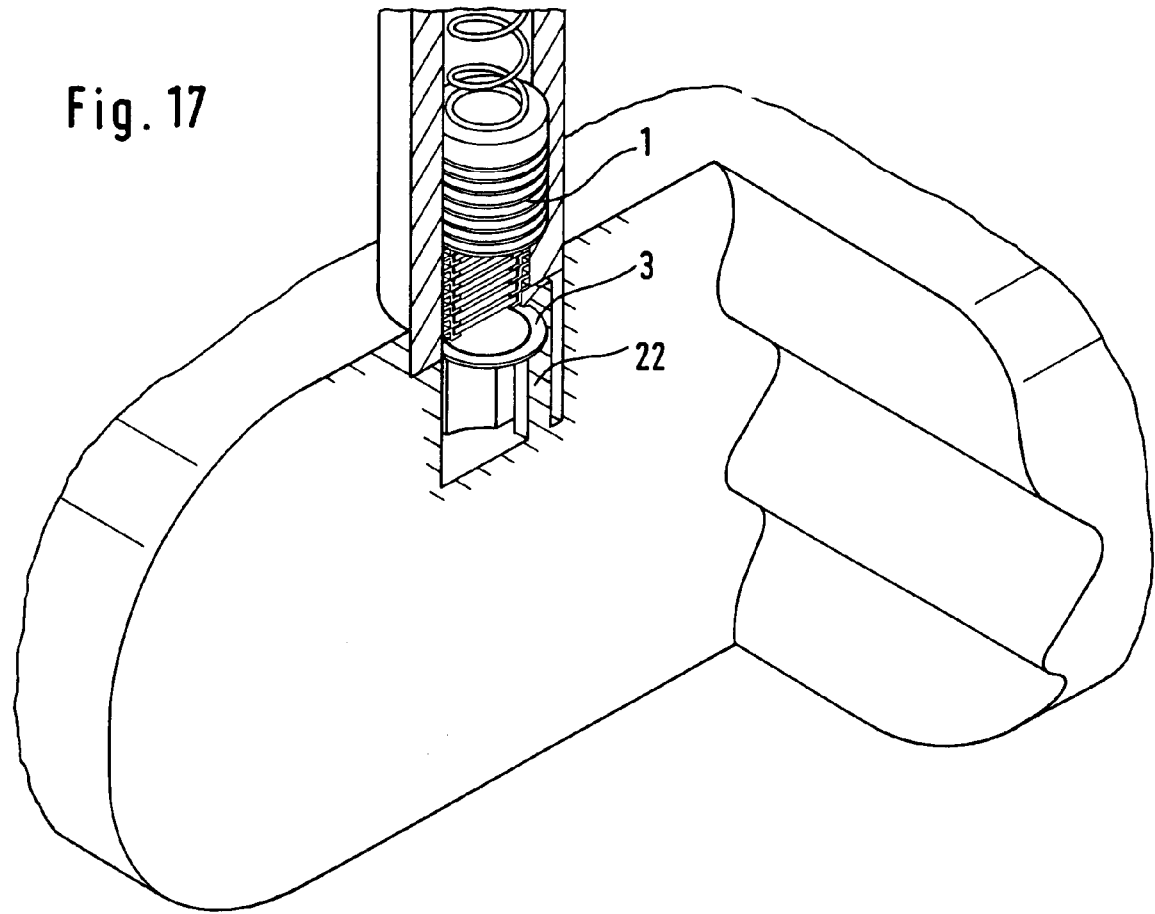
FIG. 17 shows a detailed illustration of FIG. 16.

FIGS. 15 to 17 show such a system, consisting of an evaluation instrument 60 and a magazine 32. The test element holder 61 which can be seen in FIGS. 16 and 17 includes a gripping device 20 with a plurality of gripping arms 22 (e.g. three arms). The gripping arms 22 are positioned, shaped and formed elastically, in such a manner that they grip and hold one test element 1 at a time at its frame 3, when the magazine 32 is introduced as shown into a test element aperture 62 of the evaluation instrument 60. When thereafter the magazine 32 is withdrawn (in the figures, in upward direction), the test element 1 remains in a holder formed by the gripping arms 22 and is located in a position where it can easily be contacted by the sample. Subsequently, an evaluation is performed with an evaluation device not shown here.

The production of a test element includes (in case of test elements the test field of which is produced separately from the frame) the following process steps: The frames 3 are brought into the desired profile shape, preferably by plastic deformation of a foil (preferably plastic foil, but metal foil can be used, too), in particular by stamping or by drawing; If necessary, the measuring aperture, which in case of colorimetric test elements surrounds the evaluation zone 19, is punched out simultaneously or subsequently; The test field is punched out, too, preferably taking into account the described condition with respect to the diameter $D_f$ in relation to the clear width W of the frame 3; It is advantageous to press the test field 5, by means of a plunger the outer diameter of which is smaller than the test field aperture 2, directly out of an intermediate carrier into the reception trough 40; Finally, the finished test elements are punched out of the foil, wherein the dimensions of the punching tool determine the outer limitation $D_a$ of the test elements 1.

As any person skilled in the art will recognize from the previous description and from the figures, modifications and changes can be made to the preferred embodiment of the invention without departing from the scope of the invention as defined in the following claims.

What is claimed is:

1. Test element analysis system for the analytical investigation of liquid samples, comprising:
   test elements with a test field, which for performing an analysis is brought into contact with the sample, the reaction of an analyte contained in the sample with at least one reagent contained in the test element leading to a change of a measurable variable which is characteristic for the analysis, and a test element storage container, where a plurality of test elements are stored to be taken out of the storage container at a take out position, and an evaluation instrument with a test element gripping device and a measuring device, the gripping device provided for positioning a test element in a sample application position, such that its test field is brought into contact with the sample, the measuring device being for measuring a change of a measurable variable which is characteristic for the analysis, wherein the test elements comprise a frame at least partially surrounding the substantially planar test field and including an outwardly oriented gripping rim running around the outer perimeter of the test elements, the frame having a diameter that increases from the gripping rim in both spatial directions running perpendicular to the test field plane, the gripping device, during the taking out from the storage container, holds a test element at its gripping rim.

2. Test element analysis system according to claim 1, wherein the gripping device is a part of the evaluation instrument, and wherein the test element is taken over directly from the take out position of the storage container to the evaluation unit.

3. Test element analysis system according to claim 1, the gripping device comprises a plurality of gripping arms, which are during the holding of the test element in at least point contact with the gripping rim of the test element.

4. Test element analysis system according to claim 3, wherein the arms of the gripping device are elastically moveable in such a manner that due to this elasticity they can be pushed onto the test element for holding thereof.

5. Test element analysis system according to claim 4, wherein the arms of the gripping device are part of a gripping element, which is made of a single piece of an elastically deformable material.

6. Test element analysis system according to claim 1, wherein the test element storage container comprises a magazine where the test elements are stored in a stack one upon the other.

7. Test element analysis system according to claim 2, wherein the gripping device is embodied as a gripping fork with two gripping arms, and wherein the test element is held, by means of gripping sections of the arms of the gripping fork, the gripping sections running parallel to the test field plane and being in at least point contact with the gripping rim.

8. Test element analysis system according to claim 7, wherein the distance between the arms of the gripping fork decreases towards a front end of the gripping section.

9. Test element analysis system according to claim 7, wherein the system is embodied in such a manner that one test element at a time is taken out from the test element storage container by means of a one-dimensional translatory motion of the gripping fork.

10. Test element analysis system according to claim 7, wherein the system is embodied in such a manner that the test element is transported, during at least a part of the transport path between the take out position and the sample application position, by means of a swiveling movement of the gripping fork around a fixed axis which runs vertical to the test field plane.

* * * * *